(12) United States Patent
Retsina et al.

(10) Patent No.: US 8,864,941 B2
(45) Date of Patent: *Oct. 21, 2014

(54) SEPARATION OF LIGNIN FROM HYDROLYZATE

(71) Applicant: API Intellectual Property Holdings, LLC, Atlanta, GA (US)

(72) Inventors: Thoedora Retsina, Atlanta, GA (US); Vesa Pylkkanen, Atlanta, GA (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/048,068

(22) Filed: Oct. 8, 2013

(65) Prior Publication Data

US 2014/0106426 A1   Apr. 17, 2014

Related U.S. Application Data

(63) Continuation of application No. 13/004,431, filed on Jan. 11, 2011, now Pat. No. 8,585,863, which is a continuation of application No. 12/234,286, filed on Sep. 19, 2008, now abandoned.

(51) Int. Cl.
| | |
|---|---|
| *D21C 3/06* | (2006.01) |
| *D21C 3/20* | (2006.01) |
| *D21C 11/02* | (2006.01) |
| *C07G 1/00* | (2011.01) |
| *C12P 7/04* | (2006.01) |

(52) U.S. Cl.
CPC .. *C07G 1/00* (2013.01); *D21C 3/06* (2013.01); *C12P 2201/00* (2013.01); *D21C 3/20* (2013.01); *C12P 7/04* (2013.01)
USPC ................... 162/36; 162/29; 162/77; 162/83

(58) Field of Classification Search
USPC ......................................... 162/29, 36, 77, 83
See application file for complete search history.

(56) References Cited

U.S. PATENT DOCUMENTS 4,728,727 A * 3/1988 Reintjes et al. ............... 530/500
8,585,863 B2 * 11/2013 Retsina et al. ................. 162/36

FOREIGN PATENT DOCUMENTS

WO    WO 2007146245 A2 * 12/2007

OTHER PUBLICATIONS

Smook, Handbook for Pulp and Paper Technologists, 1992, Angus Wilde Publications, 2nd edition, chapter 26.*

* cited by examiner

*Primary Examiner* — Anthony Calandra
(74) *Attorney, Agent, or Firm* — Ryan P. O'Connor

(57) ABSTRACT

A method for the production water insoluble reactive lignin having low sulfur content and lignosulfonates from lignocellulosic material in a batch or continuous process. Lignocellulosic material is fractionated to produce water insoluble native lignin and lignosulfonates in various ratios, while preserving the cellulose and hydrolyzed hemicelluloses using water, ethanol and sulfur dioxide.

17 Claims, 2 Drawing Sheets

SEPARATION OF LIGNIN FROM HYDROLYZATE

This application is a continuation of application Ser. No. 13/004,431, filed Jan. 11, 2011, now U.S. Pat. No. 8,585,863, which is a continuation of application Ser. No. 12/234,286, filed Sep. 19, 2008, now abandoned, each of which is incorporated by reference herein in its entirety.

FIELD OF THE INVENTION

This invention relates, in general, to the solvent based fractionation of lignocellulosic material and more particularly to the separation of reactive water insoluble lignin from the hydrolyzate. The lignin is precipitated after removal of solvent and by reheating the remaining liquor. Lignin can be used to as feedstock for a variety of chemical synthesis or as an end product for various applications.

BRIEF DESCRIPTION OF THE DRAWINGS

A more complete understanding of the present invention may be obtained by reference to the following detailed description when read in conjunction with the accompanying drawings wherein.

BACKGROUND OF THE INVENTION

Figure 1:
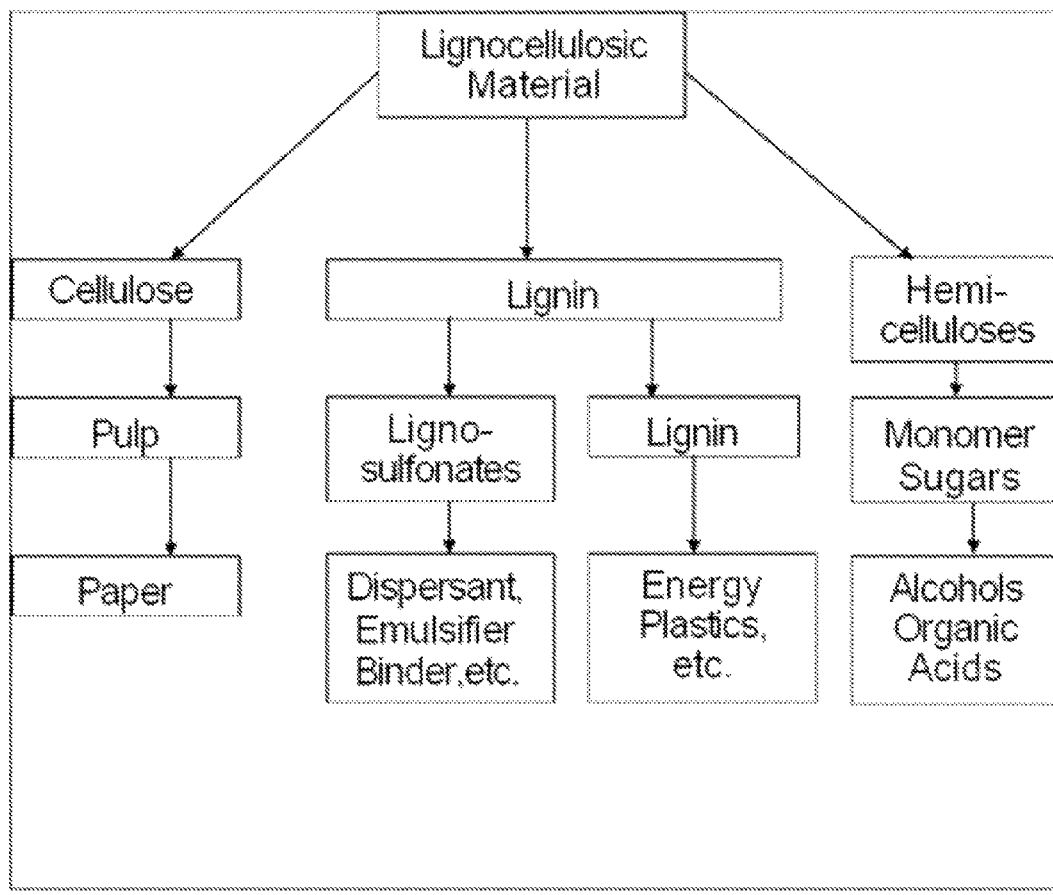
FIG. 1. illustrates the separation of lignin obtained from the solvent based hydrolysis of lignocellulosic material.
Figure 2:
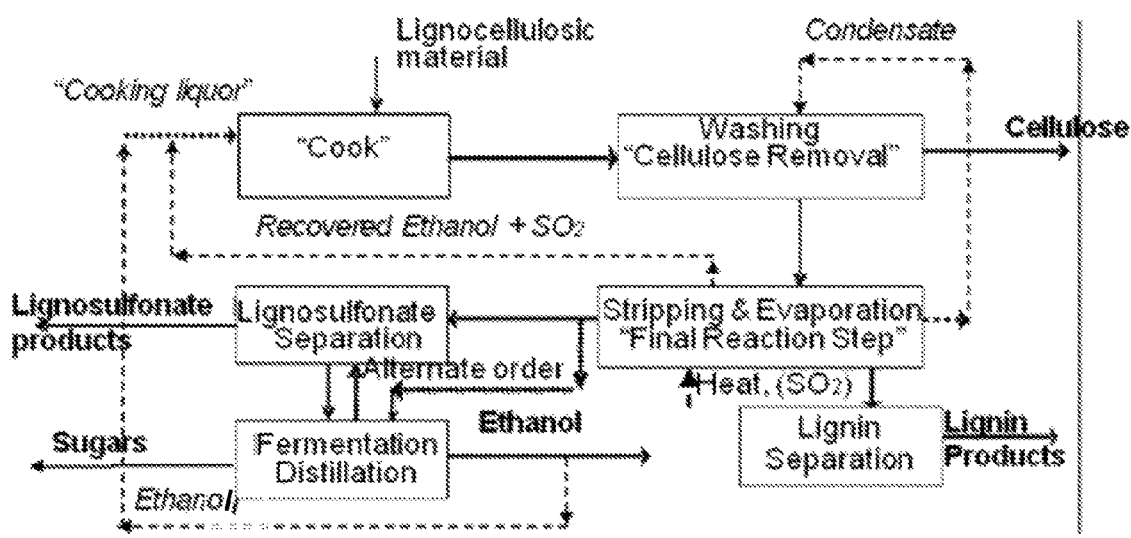
FIG. 2. illustrates a flow sheet example of the invention process, noting that the process steps may be in other sequences.

Lignin is the second most abundant organic compound on earth yet the use of lignin products is limited because of lack of manufacturing processes that readily isolate lignin in sufficient purity.

Sulfite pulping has been practiced since 1874. The early processes discharged dissolved wood sugars and lignin to rivers and streams causing significant pollution. Fermentation of sulfite liquor to hemicellulosic ethanol has been practiced, primarily to reduce the environmental impact of the discharges, from sulfite mills since 1909. The remaining spent liquor was concentrated to produce lignin rich slurry. This slurry was applied in gravel roads as a dust binder. Additional beneficial uses were developed to include surfactants, emulsion agent, dispersants, binder, etc.

The number of sulfite mills producing lignosulfonates was reduced because of new chemical recovery processes for sulfite spent liquors. Most of these processes require burning of the lignin. There are few remaining sulfite pulp mills in the world today that separate lignosulfonates, and the number of those remaining in operation continues to reduce each year. The research of beneficial uses of lignin byproduct has been reduced due to lack of available supplies.

Kraft chemical recovery pulping has eclipsed sulfite pulping as the dominant chemical pulping method. There are few commercial applications to precipitate lignin by acidifying pulping spent liquor using carbon dioxide. The recovery of Kraft pulping lignin by acid precipitation has been suggested, but Kraft lignin has undergone condensing reactions and does not possess the reactive properties of lignosulfonates.

Other processes have been suggested such as solvent pulping to produce pure lignin as a byproduct. The lignin extraction from solvent based pulping produces lignin that has not undergone significant chemical modification and is referred as "native lignin". One such demonstration size facility for ethanol-water (ALCELL) pulping produced pure lignin in the early 1990's. The product was test marketed to be used in brake pads, etc. This plant suffered from uncontrolled precipitation of "sticky" lignin, which hardened if subjected to temperatures over 75° C. There are no plants currently in operation to produce pure lignin.

Therefore in the prior art of producing lignin are:
a) The sulfite processes where base calcium, sodium, ammonia or magnesium is retained with lignosulfonate;
b) Strong and dilute acid hydrolysis processing of lignocellulosic material, where lignin is the leftover solid after hydrolyzing cellulosic parts;
c) Kraft pulping process, where lignin is precipitated by acidifying spent pulping liquor;
d) Organic solvent pulping methods, where lignin is separated by removal of solvent.

The present inventors have now developed a method wherein pure lignin can be readily produced from an organic solvent pulping or bioethanol process, This has been achieved through their experiments of organic solvent pulping with sulfur dioxide that produced lignin with unexpected properties. The lignin remained in colloidal suspension after removing the solvent and was hard to precipitate. Surprisingly, the lignin rapidly precipitated upon reheating the liquor at low pH, with and without further acidification. This precipitate filtered easily to form a whitish cake. Upon air drying the cake, the resulting lignin is a light colored powder, having a glass transient temperature at 160° C.-200° C. Furthermore, it was observed that the conditions were favorable to hydrolyze nearly all the hemicelluloses. This can be done in a batch process with a cycle time of between 0.5 and 3.5 hours, or in a continuous process.

SUMMARY OF THE INVENTION

The present invention describes a process for the production of lignin and lignosulfonates by fractionating lignocellulosic material into lignin, cellulose and hydrolyzed hemicelluloses through a staged treatment of the lignocellulosic material with a solution of aliphatic alcohol(s), water and sulfur dioxide, in a one, two or multiple step process where the cellulose is removed in an intermediary step, the hemicelluloses are converted to monomer sugars, and lignin is recovered in a solid phase. Hence in a preferred embodiment lignocellulosic material is treated in a first stage with aliphatic alcohol, water and sulfur dioxide, the cellulose is then removed, solid water insoluble lignin is removed simultaneously with alcohol recovery or sequentially by reheating liquor. The reheating of liquor causes precipitation of water insoluble lignin hydrolysis of the remaining hemicelluloses to monomeric sugars, while lignosulfonates remain soluble. Lignosulfonates can be separated from the remaining aqueous solution before or after fermenting the sugars in alcohols and organic acids.

DETAILED DESCRIPTION OF THE INVENTION

The first process step is "cooking" which fractionates the three lignocellulosic material components to allow easy downstream removal; specifically, more than 90% of lignin is dissolved, of which a portion is sulfonated in water soluble form. Lignocellulosic material is dissolved, "cooked", in reactive form in a solution of aliphatic alcohols, water, and sulfur dioxide where typical ratios are 40% to 60% of alcohol and water, and preferably 50%, and 0.05% to 30% or more of sulfur dioxide by mass; this solution is termed cooking liquor. Aliphatic alcohols can include ethanol, methanol, propanol and butanol. The cooking is performed in one or more stages using batch or continuous digesters. Depending on the lignocellulosic material to be processed, the cooking conditions are varied, with temperatures from 65° C. to 170° C. or more, for example 155° C., and corresponding pressures from 1 atmosphere to 20 atmospheres or more. The sulfur dioxide charge in the cooking liquor is varied between 0.05% and 30% or more, for example 15%, of the total cooking liquor mass in one or more cooking stages. Cooking time is also varied between 2 minutes and 210 minutes, for example 20 minutes. The wood to cooking liquor ratio is varied in between 1:2 to 1:6 or more, preferably 1:4.

Hydrolyzate withdrawn from the cooking step is subjected to pressure reduction, either at the end of a cook stage in a batch digester, or in an external flash tank after extraction from a continuous digester. The flash vapor from the pressure reduction is collected into a cooking liquor make-up vessel. The flash vapor contains substantially all the unreacted sulfur dioxide which is directly dissolved into recycled fresh cooking liquor. Part of the hydrolyzate can be recycled to cooking, while the cellulose is then removed to be washed and further treated as required.

The process washing step recovers the remaining hydrolyzate from the cellulose. The washed cellulose is pulp that can be used for paper production or other purposes. The weak hydrolyzate from the washer continues to the final reaction step; in a continuous digester application this weak hydrolyzate will be combined with the extracted hydrolyzate from the external flash tank and introduced in the lignin separation step.

The process lignin separation step is for the separation of water insoluble reactive lignin from the hydrolyzate. This step comprises of evaporation and stripping of cooking alcohol from the hydrolyzate. The evaporation process may be under vacuum or pressure from −0.1 atmosphere to 6.0 or more atmospheres, for example 1 atmosphere. Ethanol soluble lignin fraction precipitates from the hydrolyzate during the alcohol removal in the evaporation. Lignin is removed from the bottom of the stripper into a settling tank. The bottom of the tank can be separated continuously in a centrifuge and/or filter press depending on the solids settleability. The supernatant is sent back to the stripper column. Lignin product is washed with liquid and dried for commercial use. In the preferred embodiment the lignin is removed in the secondary hydrolysis step.

In the final reaction step, the remaining hydrolyzate is directly or indirectly heated to temperatures up to 150° C. or more, preferably 120° C. for 2 minutes to 120 minutes or more, preferably 60 minutes. The step may or may not include acidification of the liquor to achieve a pH of 0.1 to 3 or more, preferably pH 1. This final reaction step may be before or after evaporation, and may or may not be followed by steam stripping of the resultant hydrolyzate to remove and recover sulfur dioxide and alcohol. The lignin can be separated continuously and sent to a centrifuge and/or filter for dewatering. The hemicelluloses are converted to sugars under the conditions in the final reaction step.

In the lignosulfonate separation step, the hydrolyzate is passed through two-stage ultrafiltration step or through traditional filtration if filtration aid, lime or polyethylimine (PEI), is used. Lignosulfonates are concentrated between 20% to 60% or more solution for commercial use. The lignosulfonates step can be before or after the process fermentation and distillation step.

The process fermentation and distillation step is for the production of alcohols, most preferably ethanol, or organic acids. After removal of cooking chemicals and lignin, the hydrolyzate contains monomer sugars in water solution in which any fermentation inhibitors have been removed or neutralized. The hydrolyzate is fermented to produce dilute alcohol or organic acids, from 1% to 10% or more concentration. Alcohol from this stage is used for the cooking liquor makeup in the process cooking step and the excess alcohol is purified for saleable grade product.

The process side products removal step uses fractionation or separation techniques to remove side products from the hydrolyzate that are of economic value or accumulate to inhibit the yield and quality of the ethanol or pulp products. These side products are isolated by processing the vent from the final reaction step and the condensate from the evaporation step. Side products include furfural, methanol, and acetic acid.

Although other modifications and changes may be suggested by those skilled in the art, it is the intention of the inventors to embody within the patent warranted hereon all changes and modifications as reasonably and properly come within the scope of their contribution to the art.

Example 1

The following example illustrates the invention but in no way limits it:

Wood chips of mixed northern pine species, containing 39.7% moisture heated up and held were cooked for 10 minutes at 150° C. in a 2 liter Parr reactor. The moisture adjusted cooking liquor consisted of 15% SO2, 42.5% of ethanol and 42.5% water by weight in 6 parts of total liquor to 1 part of dry wood. Cellulose was removed and washed with water representing 47.8% of the original wood mass. The wash water was mixed and evaporated in a rotary vacuum evaporator at 85-90 degrees C. until liquor volume was half of the original and all the ethanol was evaporated. The resulting hydrolyzate, containing approximately 5% solids by weight, was put in the cold room (4° C.) centrifuged extensively in high speed centrifuge and the supernatant was removed.

The centrifuge precipitate was washed with pH 2.2 acid water and centrifuge again. washing and centrifuging was repeated for up to three times. Finally air-dry the resultant lignin was analyzed for elemental composition. The lignin consisted 1.2% sulfur, 62.8% carbon, 6.1% hydrogen, and 29.6% oxygen by weight. The empirical calculation show that the elemental composition matches closely to that of lignin precursor, coniferyl alcohol $C_{10}H_{11}O_3$, and approximately 9% of the lignin monomer units are sulfonated to empirical formula of $C_{10}H_{11}O_3SO_3$.

The centrifuge supernatant from post-evaporated liquor was treated with powdered CaO (<50 Mesh) until pH reached 11. 13.558 g of CaO is required to increase the pH of 1893.9 g concentrated liquor (4.86% solid, or 92.04 g solid) from pH 1.75 to 11. The sample was centrifuged and air-dried. The air-dried lignosulfonate was analyzed for elemental composition. The lignin consisted 3.7% sulfur, 46.5% carbon, 5% hydrogen, 37.8% oxygen and 6.9% calcium by weight. The empirical calculation shows again that the elemental composition matches closely to that of coniferyl alcohol, and approximately 39% of the lignin monomer units are sulfonated. In addition, calcium sulfate represents 11% of the total solids.

Example 2

The following example illustrates the invention but in no way limits it:

Several batches of green southern pine wood chips were cooked in a lab digester with nominal capacity of 10 liter at or below 150° C. for less than one hour. The moisture adjusted cooking liquor consisted of 12-18% SO2 by weight dissolved in 50/50 of ethanol water mixture. The liquor volume was approximately 6 parts of total liquor to 1 part of dry wood. Cellulose was removed after pulping representing 45-50% of the original wood mass. The wash water was mixed and evaporated in a rotary vacuum evaporator at 45-90° C., until liquor volume the ethanol undetectable. The resulting hydrolyzate, containing approximately was cooled in the cold room (4° C.) to room. No settling of suspended solids was observed after several days. The liquor was subjected to three treatments.

First portion (01) of the liquor was adjusted to pH 1 using concentrated sulfuric acid. The liquor was heated tot 20° C. for one hour. Precipitate was observed.

Second portion (02) of the liquor was adjusted to pH 1 using concentrated sulfuric acid. The liquor was heated to 90° C. for 10 minutes. Precipitate was observed.

Third portion (03) of the liquor had no sulfuric acid treatment after the evaporation, but yielded precipitate after heating to 90° C. for 10 minutes. Precipitate was observed.

All precipitates were filtered and washed with distilled water until pH 4 was reached. Filter cakes were air dried and sent for elemental analysis and the results are shown in the table below.

TABLE 1

| Lignin analysis results. | | | | |
| --- | --- | --- | --- | --- |
| SAMPLE ID | | 01 | 02 | 03 |
| Carbon | % | 62.43 | 62.38 | 65.71 |
| Hydrogen | % | 6.10 | 6.24 | 7.35 |
| Nitrogen | % | 0.17 | 0.17 | 0.24 |
| Oxygen (Merz) | % | 30.94 | 30.90 | 24.93 |
| Sulfur | % | 1.63 | 1.65 | 1.92 |
| HHV | BTU/lb | 11158. | 11187. | 12585. |

The table 1 shows that the sample without sulfuric acid treatment setained high carbon to oxygen ratio. This is indication of no or little reaction during the treatment. The high heating value was similar to lignin obtained by centrifuging only. Sulfuric acid appear to react with lignin and thus lower its reactivity.

What is claimed is:

1. A process for separating and recovering lignin and lignosulfonates from a liquid hydrolyzate, said process comprising:
   (a) contacting a lignocellulosic material with a solution of an aliphatic alcohol, water, and sulfur dioxide to produce a mixture comprising cellulose-rich solids and a first hydrolyzate comprising hemicellulose oligomers, lignin, and lignosulfonates;
   (b) removing said cellulose-rich solids from said mixture, to form a second hydrolyzate;
   (c) removing, in a stripper column, said aliphatic alcohol and said sulfur dioxide from said second hydrolyzate, to form a third hydrolyzate, wherein said lignin precipitates to form water-insoluble lignin;
   (d) recovering said water-insoluble lignin from said stripper column; and
   (e) separating and recovering said lignosulfonates from said third hydrolyzate.

2. The process of claim 1, wherein step (c) comprises evaporating at a pressure from −0.1 to 6.0 atmospheres in said stripper column.

3. The process of claim 1, wherein step (d) comprises removing said water-insoluble lignin from the bottom of said stripper column into a settling tank.

4. The process of claim 3, wherein step (d) further comprises centrifuging or filter-pressing said water-insoluble lignin.

5. The process of claim 1, wherein said water-insoluble lignin is continuously removed and recovered.

6. The process of claim 1, wherein step (e) comprises centrifuging said third hydrolyzate.

7. The process of claim 1, wherein said second hydrolyzate is further treated to hydrolyze said hemicellulose oligomers to monomer sugars.

8. The process of claim 1, said process further comprising fermentation of said third hydrolyzate prior to separation of said lignosulfonates.

9. The process of claim 1, said process further comprising fermentation of said third hydrolyzate following separation of said lignosulfonates.

10. A process for separating and recovering lignin and lignosulfonates from a liquid hydrolyzate, said process comprising:
    (a) contacting a lignocellulosic material with a solution of an aliphatic alcohol, water, and sulfur dioxide to produce a mixture comprising cellulose-rich solids and a first hydrolyzate comprising hemicellulose oligomers, lignin, and lignosulfonates;
    (b) removing said cellulose-rich solids from said mixture, to form a second hydrolyzate;
    (c) heating said second hydrolyzate to hydrolyze said hemicellulose oligomers to monomer sugars, wherein during said heating, said lignin precipitates to form water-insoluble lignin;
    (d) recovering said water-insoluble lignin, to form a third hydrolyzate; and
    (e) separating and recovering said lignosulfonates from said third hydrolyzate.

11. The process of claim 10, said process further comprising removing, in a stripper column, said aliphatic alcohol and said sulfur dioxide from said second hydrolyzate, wherein said stripper column is operated at a pressure from −0.1 to 6.0 atmospheres.

12. The process of claim 10, wherein step (d) comprises introducing said water-insoluble lignin into a settling tank.

13. The process of claim 12, wherein step (d) further comprises centrifuging or filter-pressing said water-insoluble lignin.

14. The process of claim 10, wherein said water-insoluble lignin is continuously removed and recovered.

15. The process of claim 10, wherein step (e) comprises centrifuging said third hydrolyzate.

16. The process of claim 10, said process further comprising fermentation of said third hydrolyzate prior to separation of said lignosulfonates from said third hydrolyzate.

17. The process of claim 10, said process further comprising fermentation of a fourth hydrolyzate following separation of said lignosulfonates from said third hydrolyzate to form said fourth hydrolyzate.

* * * * *